United States Patent [19]
Persson

[11] Patent Number: 5,643,324
[45] Date of Patent: *Jul. 1, 1997

[54] EXTERNAL DEFIBRILLATOR CIRCUIT

[75] Inventor: Eric Persson, Minnetonka, Minn.

[73] Assignee: SurvivaLink Corporation, Minneapolis, Minn.

[*] Notice: The term of this patent shall not extend beyond the expiration date of Pat. No. 5,405,361.

[21] Appl. No.: 419,373

[22] Filed: Apr. 10, 1995

Related U.S. Application Data

[63] Continuation of Ser. No. 31,532, Mar. 15, 1993, Pat. No. 5,405,361.

[51] Int. Cl.⁶ ............................................. A61N 1/39
[52] U.S. Cl. ......................................................... 607/5
[58] Field of Search .................................. 607/4, 5, 7, 10, 607/12

[56] References Cited

U.S. PATENT DOCUMENTS

| | | |
|---|---|---|
| 3,706,313 | 12/1972 | Milani et al. |
| 3,886,950 | 6/1975 | Ukkestad. |
| 4,050,004 | 9/1977 | Greatbach. |
| 4,566,457 | 1/1986 | Stemple. |
| 4,823,796 | 4/1989 | Benson. |
| 5,385,575 | 1/1995 | Adams ............................................ 607/5 |
| 5,405,361 | 4/1995 | Persson ........................................... 607/5 |
| 5,507,781 | 4/1996 | Kroll et al. ...................................... 607/7 |

FOREIGN PATENT DOCUMENTS

| | | |
|---|---|---|
| 2589462 | 7/1964 | Australia. |
| 0445800 | 9/1991 | European Pat. Off.. |
| 0487776 | 6/1992 | European Pat. Off.. |

*Primary Examiner*—Jeffrey R. Jastrzab
*Attorney, Agent, or Firm*—Patterson & Keough, P.A.

[57] ABSTRACT

A portable, automatic external defibrillator, comprising a plurality of capacitors; a capacitor charging circuit; connections from the capacitors to a patient body; and a plurality of semiconductor switches arranged to connect the capacitors to the charging circuit and to the patient body.

4 Claims, 4 Drawing Sheets

EXTERNAL DEFIBRILLATOR CIRCUIT

CROSS-REFERENCE TO RELATED APPLICATION

This application is a continuation of U.S. patent application Ser. No. 08/031,532, filed Mar. 15, 1993, now U.S. Pat. No. 5,405,361, which is incorporated herein by reference.

BACKGROUND OF THE INVENTION

1. Field of the Invention

This invention relates to medical therapeutic apparatus. More particularly, this invention relates to electronic circuitry for use in an external defibrillator apparatus. The apparatus of this invention provides an improved, low cost, portable external defibrillator.

2. Background Information

The external defibrillator is a well recognized and important tool for resuscitating cardiac arrest patients. Defibrillation of the human heart is accomplished by applying an electrical waveform to the cardiac muscle with appropriate electrodes, causing the cessation of rapid uncoordinated contractions of the heart (fibrillation) and restoration of normal beating of the heart.

In the past, external defibrillators have been limited in use to hospitals, ambulances and other specialized locations. However, the health care community has recently called for more widespread disposition and use of automatic external defibrillators, particularly those which are portable. For example, it has been recognized that the placement of portable external defibrillators in nursing homes, sports facilities, and various other public and private facilities could save many lives in the setting of a cardiac arrest. Another proposal for the widespread placement of portable external defibrillators is with public safety officials such as police squad cars and the like.

A primary factor in limiting the dissemination of portable external defibrillators is their cost. A typical portable external defibrillator costs approximately $5,000 to 10,000. Costs for portable external defibrillators are high mainly due to the high costs of circuit components which are able to deal with extremely high voltages and currents utilized in cardiac defibrillation.

Despite the need in the art for a portable external defibrillator apparatus and circuitry therefor which overcomes the limitations and problems of the prior art, none insofar as is known has been proposed or developed. Accordingly, it is an object of the present invention to provide a portable automatic external defibrillator apparatus which overcomes the limitations and shortcomings of the prior art. Particularly, it is an object of this invention to provide an improved portable external defibrillator apparatus which is reliable, durable, and effective at delivering defibrillating charges to the body of a patient. Another object of this invention is to provide defibrillation circuitry which is inexpensive to construct so that portable external defibrillators may be disseminated in a variety of settings and locations and for use by a variety of skilled and semiskilled medical personnel. A specific object of this invention is to provide circuitry for charging a plurality of capacitors in parallel and for discharging them in series which utilizes a plurality of semiconductor switches.

SUMMARY OF THE INVENTION

In a basic aspect, the present invention provides a defibrillator apparatus, comprising:

(a) a plurality of capacitors;

(b) means to charge the capacitors;

(c) means to connect the capacitors to a patient; and (d) first and second switch sets for independently switching the capacitors between the charge means and the means to connect, to thereby charge and discharge the capacitors, each switch set including a plurality of semiconductor switch elements, the first switch set being connected to the capacitors and arranged to charge the capacitors in parallel the second switch set being connected to the capacitors and arranged to discharge the capacitors in series, simultaneously.

In another aspect, the invention provides a defibrillator apparatus, comprising:

(a) a plurality of capacitors selectively connected in parallel with each other;

(b) means to charge the capacitors;

(c) means to connect the capacitors to a patient;

(d) first and second switch sets for independently switching the capacitors between the charge means and the means to connect, to thereby charge and discharge the capacitors, each switch set including a plurality of semiconductor switch elements, the first switch set being arranged so that the capacitors charge in parallel, and the second switch set being arranged so that the capacitors discharge in series, simultaneously; and (e) a third semiconductor switch set including a plurality of semiconductor switch elements, each being disposed across a respective the capacitor for dumping charge from the capacitors at a predetermined time.

In yet another aspect, the invention provides a portable external defibrillator apparatus, comprising:

(a) "x" number of capacitors, where "x" is greater than 1, selectively connected in parallel with each other, each capacitor having first and second electrodes;

(b) means to charge the capacitors;

(c) at least two medical connection electrodes, communicatively connected to the capacitors via conductive leads, and for placement on the body of a patient;

(d) a charge path formed by the capacitors further comprising "x−1" number of first semiconductor switches disposed in series with each other, each between the first electrode of a capacitor "n" and the first electrode of a capacitor "n+1", the charge path charging the capacitors in parallel;

(e) a discharge path, independent of the charge path, formed by the capacitors and further comprising "x" number of second semiconductor switches disposed in series with each other, each between the second electrode of the capacitor "n" and the first electrode of the capacitor "n+1," the discharge path discharging the capacitors in series, simultaneously; and (f) "x" number of diodes disposed in series with each other, each being disposed between the second electrode of the capacitor "n" and the second electrode of capacitor "n+1".

The benefits and objects of this invention will become clear from the following description by reference to the drawings.

DESCRIPTION OF THE PREFERRED EMBODIMENT

Figure 1:
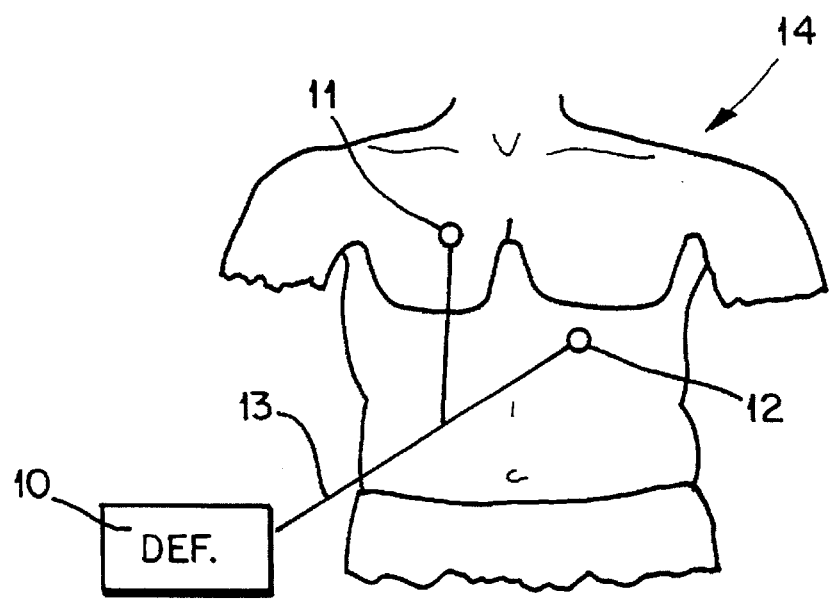
FIG. 1 is a simplified diagram showing the operative connection of a typical portable external defibrillator to the chest region of a patient.
Figure 2:
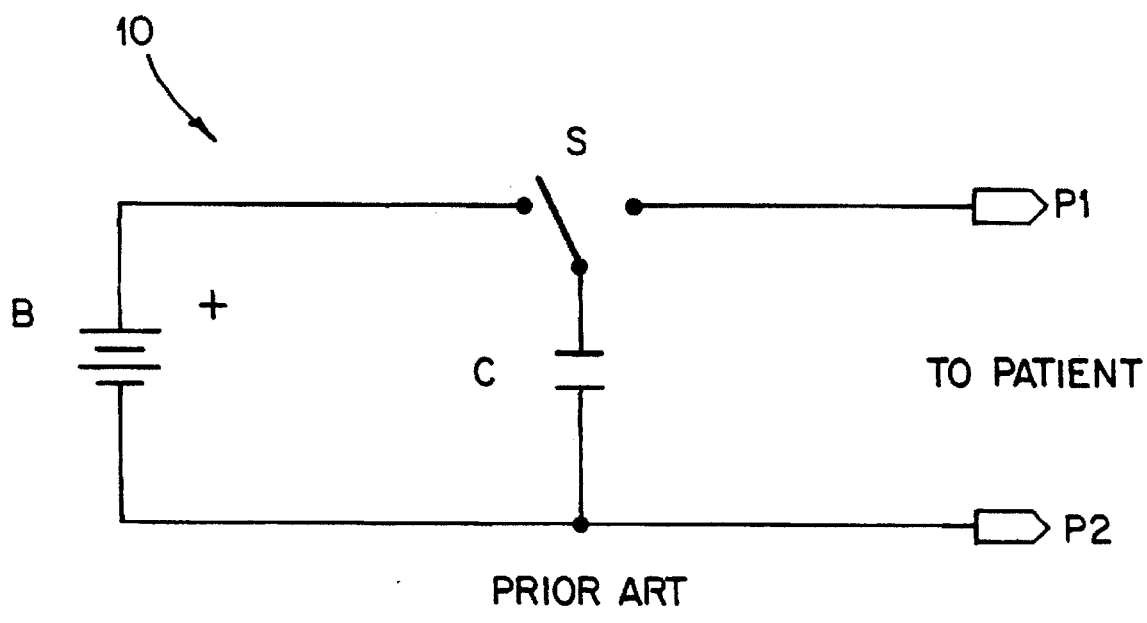
FIG. 2 is a simplified schematic diagram of a prior art defibrillator circuit.

Referring to FIGS. 1 and 2, the external defibrillator 10 is electrically linked to at least two electrodes 11 and 12 via a cable set 13. The electrodes 11 and 12 are shown operatively disposed on the chest region of a patient 14. FIG. 2 shows a simplified version of the internal circuitry of a prior art external defibrillator 10. Basically, the circuit comprises a battery based power source B connected to a capacitor or other charge storage element or circuit C and a switch S which enables connection of the battery B to the capacitor C during a charge accumulation state, and connection of the capacitor C to the electrodes 11 and 12 during a discharge state where fie stored charge is being delivered to the patient body 14 for cardiac defibrillation purposes.

In prior art defibrillators, the capacitor and switch are the two components of the device which contribute most significantly to the overall cost of manufacture. The defibrillator must be able to discharge a large amount of energy, on the order of 400 Joules, in order to reliably defibrillate the patient. Prior art defibrillators have met this requirement by utilizing a single, rather large capacitor. The cost of such a component is significant. Also due to the relatively high voltages and currents involved, the potential for leakage voltages, and because of reliability constraints, prior art defibrillators typically utilize mechanical relay devices for switching. These components are also costly. As was previously discussed, cost factors have heretofore made it very difficult to disseminate portable external defibrillators on a widespread basis.

Figure 3:
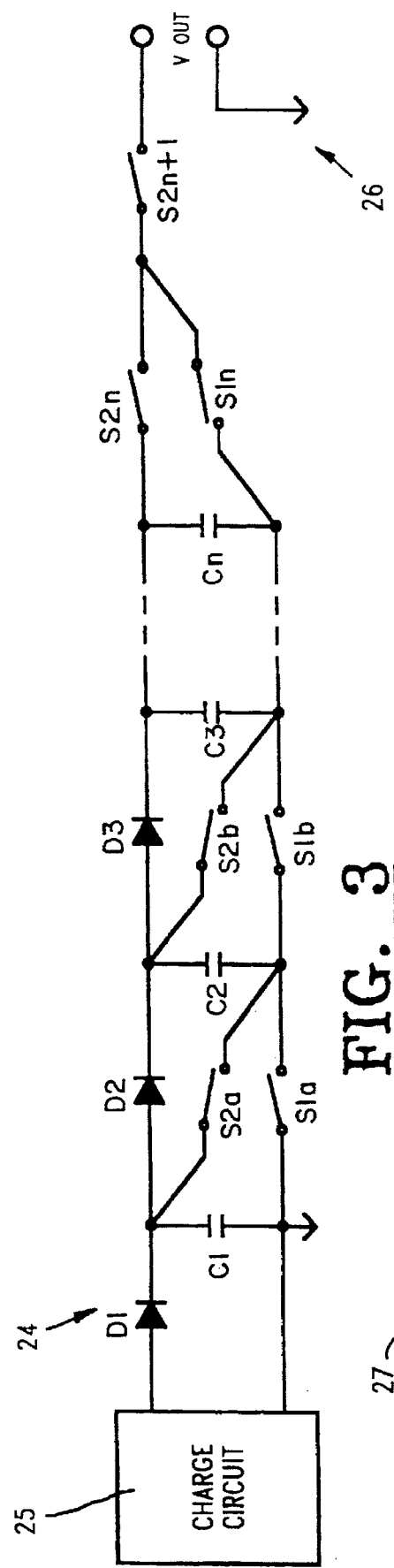
FIG. 3 is a simplified schematic diagram of one embodiment of the defibrillator circuit of the present invention.

Referring to FIG. 3, a basic embodiment of circuitry 24, of the present invention, for a portable external defibrillator is shown comprising a plurality of semiconductor switch elements S in conjunction with a charging circuit 25 and capacitors C. Semiconductor devices such as silicone-controlled rectifiers (SCR's) are commonly available at a relatively low cost. A plurality of 400 to 1200V thyristors may be utilized for example to control switching from charge and discharge states in the defibrillator. These components are mass produced for devices such as light dimmer itches and may thus be obtained inexpensively.

The circuit 24 comprises a plurality of capacitors C(1-n), preferably six, connected to a charging circuit 25 and selectively in parallel with respect to each other. The capacitor charging circuit 25 is a current limited voltage source. Small, approximately 400V capacitors are also mass produced for energy storage in camera flash system and the like, and are thus inexpensive to obtain. The configuration of the capacitors C in parallel eliminates the voltage imbalance problem inherent in charging electrolytic capacitors in series. For convenience of reference, the electrodes or terminals of capacitors C(1-n) are designated "second" (positive) at the top end of the circuit 24, and "first" (negative) at the bottom end of the circuit 24.

Still referring to FIG. 3, the circuit 24 is constructed and arranged to allow for the charging of the capacitors C(1-n) in parallel and for discharge in series to deliver required high voltage defibrillating shocks. This is accomplished via the utilization of first semiconductor switches S1(a-n) and second S2(a-n), primarily.

Five switches S1(a-n) are disposed in series with respect to each other, each individual switch S1n being disposed between the first electrode of each individual capacitor Cn and the first electrode of its adjacent capacitor Cn+1. The first electrode of capacitor C1 is shown to be connected to ground. Six switches S2(a-n) are disposed essentially in series with each other, each individual switch S2n being disposed between the second electrode of each individual capacitor Cn and the first electrode of its adjacent capacitor Cn+1. When switches S1(a-n) are turned on the capacitors C are connected in parallel.

The last switch S2n in the series is shown to be connected between the first electrode of the last capacitor Cn in the circuit 24 and the output section 26 of the circuit 24. When switches S2(a-n) are turned on the capacitors C are now effectively in series, with the sum of their voltage appearing at Vout.

A plurality of diodes D(1-n) are connected in series with each other, the anodes of which are disposed towards the capacitor charging circuit 25. Diode D1 is disposed between the charging circuit 25 and the second electrode of capacitor C1. The remaining diodes D2-Dn are disposed between the second electrode of each capacitor Cn and the second electrode of its adjacent capacitor Cn+1. These diodes allow for parallel charging of the capacitors C, and become reversed biased when switches S2(a-n) are turned on.

In a charge-up state, itches S2(a-n) are open and switches S1(a-n) are closed. The capacitors C1-n charge in parallel. Switches S1 can be implemented by an optocoupled transistor, such as that shown in FIG. 5A as OP1, for example. No component of this circuit 24 will see a voltage higher than the voltage present on one capacitor C. As a result, where this circuit 24 has six capacitors C and a peak circuit 24 output of approximately 2000V, no capacitor C will see more than approximately 333 volts. This allows the use of relatively inexpensive components having the same breakdown voltage of approximately 400V. Each capacitor Cn+1 has one (1) diode drop less voltage than its adjacent capacitor Cn. An additional benefit of this low voltage circuit configuration is that leakage currents, which are inherent in semiconductor components and on the circuit boards, for example, at high voltages, are minimized.

During discharge to a patient, switches S2(a-n) are closed and switches S1(a-n) are open. The capacitors C1-n thus discharge in series, delivering current to the patient's heart. Switches S2 can be implemented via a variety of semiconductor means, but a thyristors, triac or transistor are preferred for cost reasons. Triggering of these itches S2(a-n) is accomplished via a galvanically isolated circuit. Triggering is preferably accomplished magnetically via gate drive transformers to simultaneously trigger switches S2. An optically coupled SCR or triac may alternatively be used.

Figure 4:
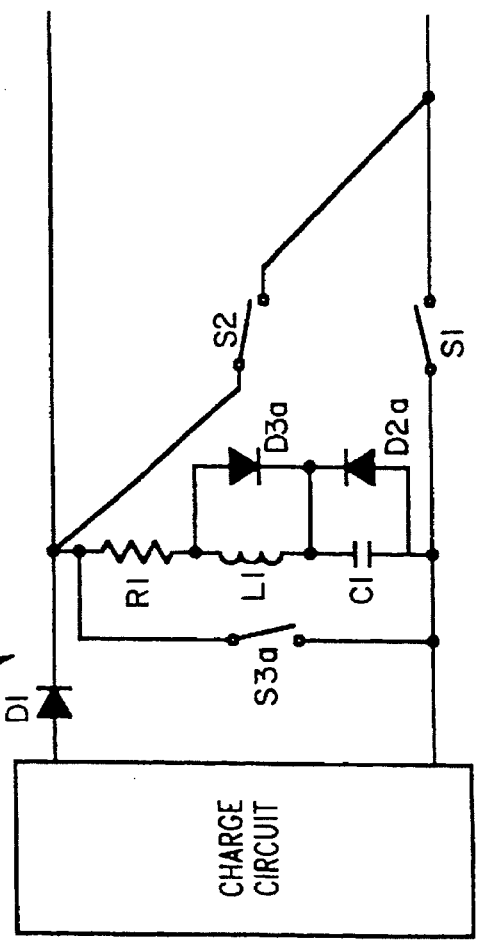
FIG. 4 is a schematic diagram of a portion of an alternative embodiment of the defibrillator circuit of this invention.

Referring to FIG. 4, a segment 27 of a preferred circuit embodiment is shown. Current limit and rise time limit in the switches S2 is implemented by placing a resistor R1 and an inductor L1 in series with each capacitor Cn. Additionally, a parallel dump switch S3 is shown added across the network C1/L1/R1 to deliver an appropriate defibrillation waveform with a rapid drop in voltage at a predetermined time. This is particularly important when thyristors, which are difficult to mm off; are utilized in itching. A clamp diode D2(a-n) is added across each capacitor Cn to prevent that capacitor Cn from becoming reverse biased. In addition, a flyback diode D3(a-n) may be included across each inductor Ln if a power transistor, which can be mined off as well as on, is used in the circuit.

Figure 5A:
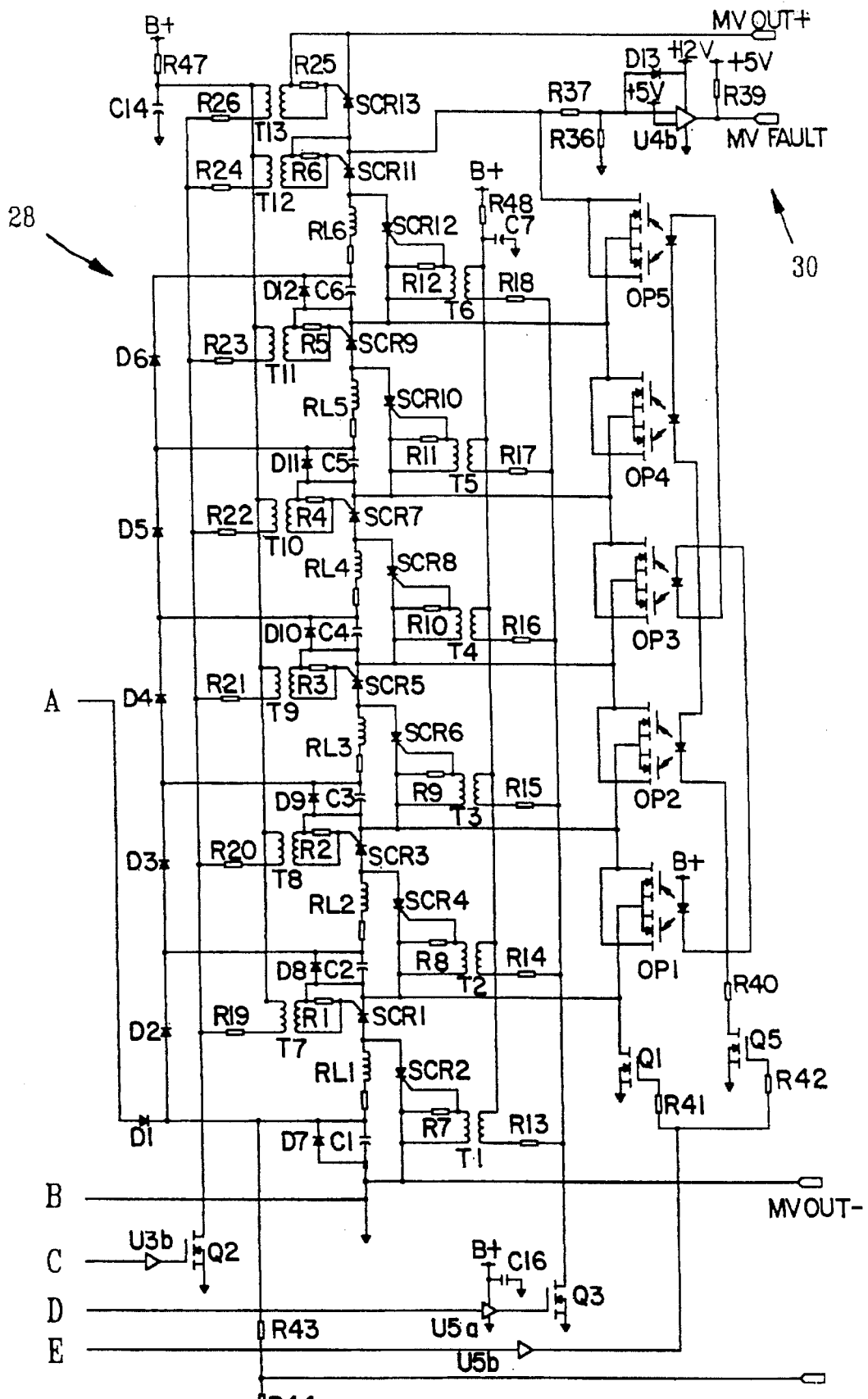
FIGS. 5A and 5B are a schematic diagram of the most preferred embodiment of the defibrillator circuit of this invention.
Figure 5B:
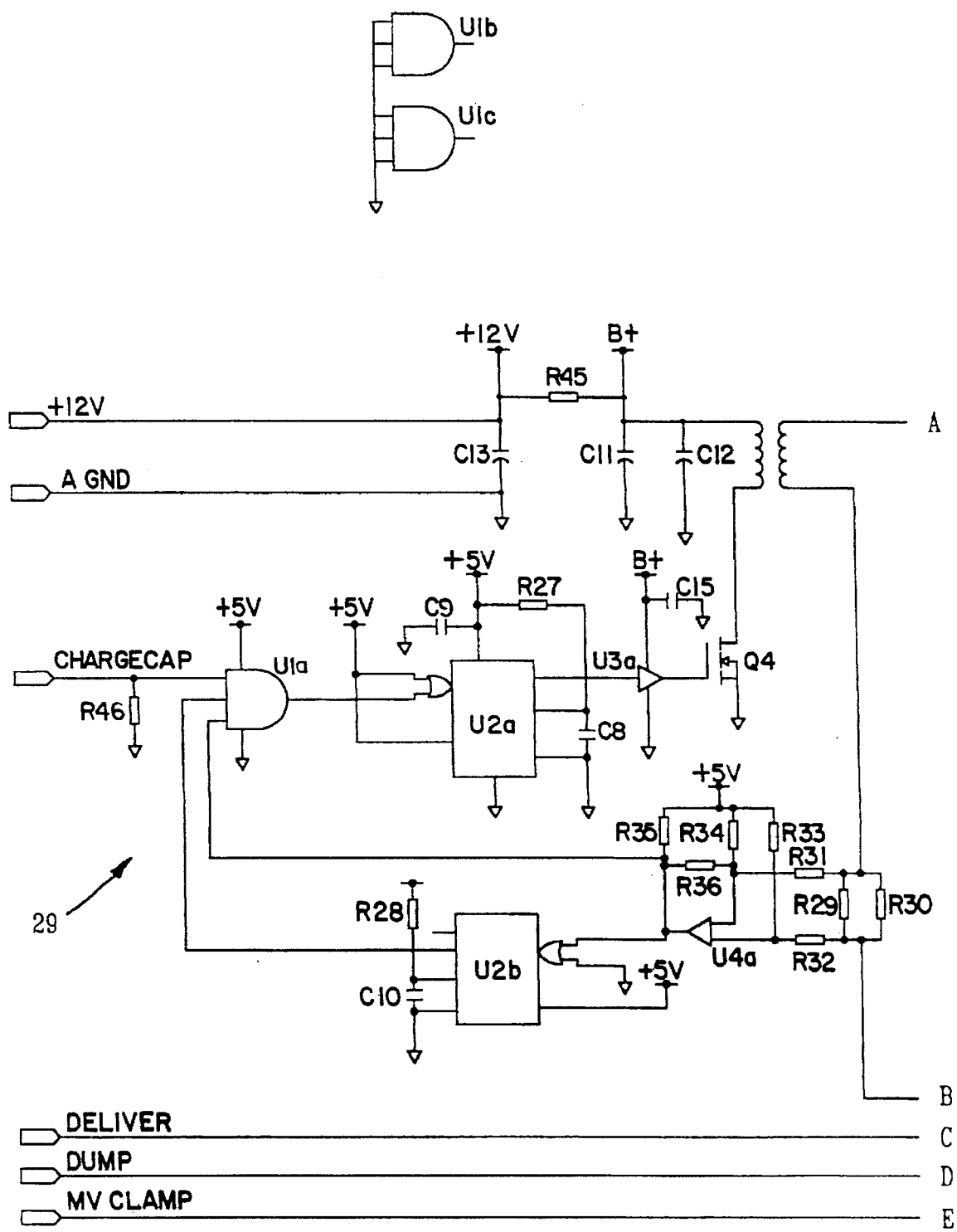

Referring to FIGS. 5A and 5B, the most preferred circuit embodiment 28 of this invention basically comprises a voltage converter circuit 29, six capacitors C1–6 connected in parallel with one another with respect to HV OUT "+" and "–". Seven diodes D1–7 are connected in series, each between first electrodes of the capacitors C1–6. First semiconductor switches Q1,OP1,2,3, and 4 are connected in series, each between second electrodes of adjacent capacitors C1–6. The first semiconductor switches OP1,2,3, and 4 are shown to be optocoupled transistors, and Q1 is a conventional FET. Op5 is an additional switch which is used to shunt any leakage currents. Second semiconductor switches SCR1,3,5,7,9 and 11 are connected between the first and second electrodes of adjacent capacitors C. Second switches SCR 1,3,5,7,9 and 11 are shown to be magnetically triggered SCR's. As was previously discussed, the essential characteristic in the behavior of this circuit 28 is that the capacitors C1–6 charge in parallel via closure of first switches Q1,OP1,2,3, and 4, and discharge in series via closure of second switches SCR1,3,5,7,9 and 11.

Capacitor C1 preferably has a resistor R1 and an inductor L1 (combination RL1) disposed in series with it. The remaining capacitors C2–6 are similarly configured with RL networks to limit peak current and rise time in itches SCR1,3,5,7,9 and 11 during an output, or switches SCR2, 4,6,8,10 and 12 during a dump. Clamp diodes D7,8,9,10,11 and 12 are also shown disposed with respect to these capacitors. Finally, switches SCR2,4,6,8, 10, and 12 are shown disposed in parallel across capacitor networks C1–6, respectively, to dump charge at a predetermined time in the discharge cycle. Preferably, switches SCR2,4,6,8,10 and 12 are magnetically triggered SCR's.

SCR 13 is shown disposed at the final node anterior to HV Out(+) to prevent leakage of DC current upon capacitor charge up. SCR 13 is triggered simultaneously with SCR1, 3,5,7,9 and 11 and serves as a redundant switch to minimize leakage currents to the patient when capacitors are charged.

The descriptions above and the accompanying drawings should be interpreted in the illustrative and not the limited sense. While the invention has been disclosed in connection with the preferred embodiment or embodiments thereof; it should be understood that there may be other embodiments which fall within the spirit and scope of the invention as defined by the following claims. Where a claim is expressed as a means or step for performing a specified function it is intended that such claim be construed to cover the corresponding structure, material, or acts described in the specification and equivalents thereof, including both structural equivalents and equivalent structures.

The invention claimed is:

1. An external defibrillator high voltage circuit for generating defibrillation pulses, including:

a pair of electrodes;

a charging power source having first and second charge supply terminals;

first and second output terminals configured for electrical interconnection to the electrodes;

first and second charge supply terminals configured for electrical interconnection to a charging voltage supply;

N capacitors $C_n$ where N is at least 2 and n=1 ... N, for storing electrical energy, each capacitor having first and second terminals, and the first terminal of capacitor $C_1$ electrically coupled to the second charge supply terminal of the charging power source;

a plurality of diodes, including a diode interconnected between the second terminals of capacitors $C_n$ and $C_{n+1}$ for each of the N capacitors;

a plurality of charging semiconductor switches for interconnecting the first terminals of the N capacitors to the first charge supply terminal and simultaneously electrically interconnecting each of the N capacitors in a parallel circuit between the first and second charge supply terminals of the charging power Source to charge the capacitors to the charging voltage when switched to an electrically closed state, and electrically isolating the capacitors from each other when switched to an electrically open state;

a plurality of discharging semiconductor switches for interconnecting the second terminal of the capacitor $C_n$ and the first terminal of the capacitor $C_{n+1}$ for each of the N capacitors and simultaneously electrically interconnecting each of the N capacitors in a series circuit between the first and second output terminals to produce defibrillation pulses when switched to an electrically closed State, and electrically isolating the capacitors from each other when switched to an electrically open state; and a charge dump circuit, including one or more charge dump semiconductor switches in a charge dump current flow path, for simultaneously discharging each of the N capacitors when the charge dump semiconductor switches are switched to an electrically closed state and further including a charge dump semiconductor switch in parallel with each of the N capacitors.

2. The external defibrillator high voltage circuit of claim 1 wherein the charge dump semiconductor switches include silicon controlled rectifiers.

3. The external defibrillator high voltage circuit of claim 2 and further including isolation circuits for coupling the charge dump control signals to the charge dump semiconductor switches.

4. The external defibrillator high voltage circuit of claim 3 wherein the isolation circuits include transformers.

* * * * *